US00PP14488P29

(12) United States Plant Patent
Covington

(10) Patent No.: US PP14,488 P2
(45) Date of Patent: Jan. 27, 2004

(54) LANTANA PLANT NAMED 'SONSHINE'

(50) Latin Name: *Lantana camara*
Varietal Denomination: Sonshine

(75) Inventor: James S. Covington, Clinton, MS (US)

(73) Assignee: Clinton Nursery, Inc., Clinton, MS (US)

( * ) Notice: Subject to any disclaimer, the term of this patent is extended or adjusted under 35 U.S.C. 154(b) by 0 days.

(21) Appl. No.: 10/313,154

(22) Filed: Dec. 6, 2002

(51) Int. Cl.[7] ..... A01H 5/00
(52) U.S. Cl. ..... Plt./227
(58) Field of Search ..... Plt./227

*Primary Examiner*—Kent Bell
(74) *Attorney, Agent, or Firm*—C. A. Whealy

(57) ABSTRACT

A distinct cultivar of Lantana plant named 'Sonshine', characterized by its mounded and outwardly spreading plant habit; freely branching growth habit; freely flowering habit; bright yellow-colored flowers; and excellent garden performance.

1 Drawing Sheet

Botanical classification/cultivar designation: *Lantana camara* cultivar Sonshine.

BACKGROUND OF THE INVENTION

The present Invention relates to a new and distinct cultivar of Lantana plant, botanically known as *Lantana camara*, and hereinafter referred to by the cultivar name Sonshine.

The new Lantana originated from a cross-pollination during the spring of 2000 of the *Lantana camara* cultivar Sonrise, disclosed in U.S. Plant Pat. No. 10,856, as the female, or seed, parent with an unidentified selection of *Lantana camara*, not patented, as the male, or pollen, parent. The cultivar Sonshine was discovered and selected by the Inventor as a single plant within the progeny of the stated cross-pollination in a controlled environment in Clinton, Miss. during the summer of 2000.

Asexual reproduction of the new cultivar by terminal cuttings taken in Clinton, Miss., since the fall of 2000, has shown that the unique features of this new Lantana are stable and reproduced true to type in successive generations.

SUMMARY OF THE INVENTION

Plants of the cultivar Sonshine have not been observed under all possible environmental conditions. The phenotype may vary somewhat with variations in environment and culture such as temperature and light intensity without, however, any variance in genotype.

The following traits have been repeatedly observed and are determined to be the unique characteristics of 'Sonshine'. These characteristics in combination distinguish 'Sonshine' as a new and distinct cultivar:

1. Mounded and outwardly spreading plant habit.
2. Freely branching growth habit.
3. Freely flowering habit.
4. Bright yellow-colored flowers.
5. Excellent garden performance.

Plants of the new Lantana differ from plants of the female parent, the cultivar Sonrise, in the following characteristics:

1. Plants of the new Lantana are shorter than plants of the cultivar Sonrise.

2. Plants of the new Lantana have bright yellow-colored flowers whereas plants of the cultivar Sonrise have golden yellow-colored flowers that become various shades of orange to red, hot pink and eventually purple during development.

Plants of the new Lantana can be compared to plants of the cultivar Samson, disclosed in U.S. Plant Pat. No. 12,705. However, in side-by-side comparisons conducted by the Inventor in Clinton, Miss., plants of the new Lantana differed from plants of the cultivar Samson in the following characteristics:

1. Plants of the new Lantana were more spreading and more vigorous than plants of the cultivar Samson.
2. Plants of the new Lantana had bright yellow-colored flowers whereas plants of the cultivar Samson had golden yellow and orange-colored flowers.

Plants of the new Lantana can also be compared to plants of the cultivar New Gold, not patented. However, in side-by-side comparisons conducted by the Inventor in Clinton, Miss., plants of the new Lantana differed from plants of the cultivar New Gold in the following characteristics:

1. Plants of the new Lantana were taller, more spreading and more vigorous than plants of the cultivar New Gold.
2. Plants of the new Lantana had bright yellow-colored flowers whereas plants of the cultivar New Gold had golden yellow-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Lantana.

The photograph at the top of the sheet comprises a side perspective view of a typical two-year old flowering plant of 'Sonshine' grown in the ground.

The photograph at the bottom of the sheet comprises a close-up view of typical flowers and leaves of 'Sonshine'.

DETAILED BOTANICAL DESCRIPTION

In the following description, color references are made to The Royal Horticultural Society Colour Chart, 1995 Edition, except where general terms of ordinary dictionary significance are used. Plants were grown in 1.5-gallon containers and under outdoor conditions in Clinton, Miss. during the summer. Plants were about two years old when the description was taken.

Botanical classification: *Lantana camara* cultivar Sonshine.

Parentage:

*Female, or seed, parent.*—*Lantana camara* cultivar Sonrise, disclosed in U.S. Plant Pat. No. 10,856.

*Male, or pollen, parent.*—Unidentified selection of *Lantana camara*, not patented.

Propagation:

*Type cutting.*—Terminal cuttings.

*Time to initiate roots, summer.*—About 7 days at 32° C.

*Time to initiate roots, winter.*—About 14 days at 18° C.

*Time to develop roots, summer.*—About 45 days at 32° C.

*Time to develop roots, winter.*—About 70 days at 18° C.

*Root description.*—Numerous, fibrous and well-branched.

Plant description:

*Form.*—Perennial flowering plant; subshrub; initially upright, then outwardly spreading, mounded. Freely branching; lateral branches potentially forming at every node; pinching enhances lateral branch development.

*Plant height.*—About 42 cm.

*Plant diameter.*—About 68 cm.

*Vigor.*—Moderately vigorous to vigorous.

*Lateral branches.*—Length: About 48 cm. Diameter: About 4 mm. Internode length: About 3.3 cm. Aspect: Initially upright, then bending about 45 to 90° from upright. Strength: Flexible, but strong. Texture: Pubescent; fine white hairs; coarse. Color: Young: Close to 144A. Woody: Close to 199A.

*Foliage description.*—Arrangement: Opposite, simple. Length: About 5.7 cm. Width: About 4.5 cm. Shape: Ovate. Apex: Acute. Base: Obtuse. Margin: Crenate to serrate. Texture: Rough, coarse; pubescence on both surfaces; rugose. Fragrance: Pungent, herb-like. Color: Young foliage, upper surface: 147A. Young foliage, lower surface: 147B. Mature foliage, upper surface: Darker than 147A. Mature foliage, lower surface: 147B. Veins, upper surface: 147A to 147B. Veins, lower surface: 147B. Petiole length: About 1.25 cm. Petiole diameter: About 2 mm. Petiole color: Close to 146A.

Flower description:

*Flower type and habit.*—Small salverform flowers arranged in axillary umbels; flowers face mostly upward or outward. Flowers self-cleaning. Very freely flowering with potentially two inflorescences per node; typically about 30 flowers per umbel.

*Natural flowering season.*—Spring until frost in the autumn; flowering continuous.

*Flower longevity on the plant.*—About one week.

*Fragrance.*—Faint, sweet, pleasant.

*Inflorescence diameter.*—About 3.5 cm.

*Inflorescence height.*—About 1.5 cm.

*Flowers.*—Appearance: Flared trumpet, corolla fused, four-parted; flowers roughly rectangular in shape. Diameter: About 1 cm by 8 mm. Corolla tube length: About 9 mm.

*Flower buds* (*just before showing color*).—Length: About 3 mm. Diameter: About 2 mm. Shape: Oblong. Color: 146A to 146B.

*Petals.*—Arrangement/appearance: Single whorl of four petals, fused into flared trumpet. Length from throat: Upper petal, about 5 mm; lower and lateral petals, about 4 mm. Width: Upper petal and lower petal, about 7 mm; lateral petals, about 6 mm. Shape: Upper and lower petals, somewhat spatulate; lateral petals, mostly orbicular. Apex: Rounded. Base: Fused. Margin: Entire. Texture, upper and lower surfaces: Smooth, satiny; throat, whiskered. Color: When opening and fully opened, upper surface: Close to 12A. When opening and fully opened, lower surface: Close to 11A.

*Sepals.*—Arrangement/appearance: One per flower arranged in a spiral whorl; leaf-like. Length: About 5 mm. Width: About 1.75 mm. Shape: Linear. Apex: Sharply acute. Margin: Entire. Texture: Pubescent. Color, upper and lower surfaces: 146A.

*Peduncles.*—Length: About 3.75 cm. Diameter: About 1.25 mm. Angle: About 30 to 45° to the stem. Strength: Flexible, but strong. Color: 144A.

*Pedicels.*—Length: Less than 1 mm. Diameter: Less than 1 mm. Color: Close to 144A.

*Reproductive organs.*—Stamens: Quantity: About four. Anther shape: Oblong. Anther length: Less than 1 mm. Anther color: Dark yellow. Pollen amount: None observed. Pistils: Quantity: One. Pistil length: Less than 1 mm. Stigma color: Close to 144A. Style color: 144D. Ovary color: 144A.

*Fruit/seed.*—Fruit and seed production has not been observed.

Disease/pest resistance: Plants of the new Lantana have not been noted to be resistant to pathogens and pests common to Lantana.

Weather tolerance: Plants of the new Lantana have been observed to be tolerant to rain, wind and to temperatures above 43° C., and hardy to at least zone 8 (USDA Hardiness Zone).

It is claimed:

1. A new and distinct cultivar of Lantana plant named 'Sonshine', as illustrated and described.

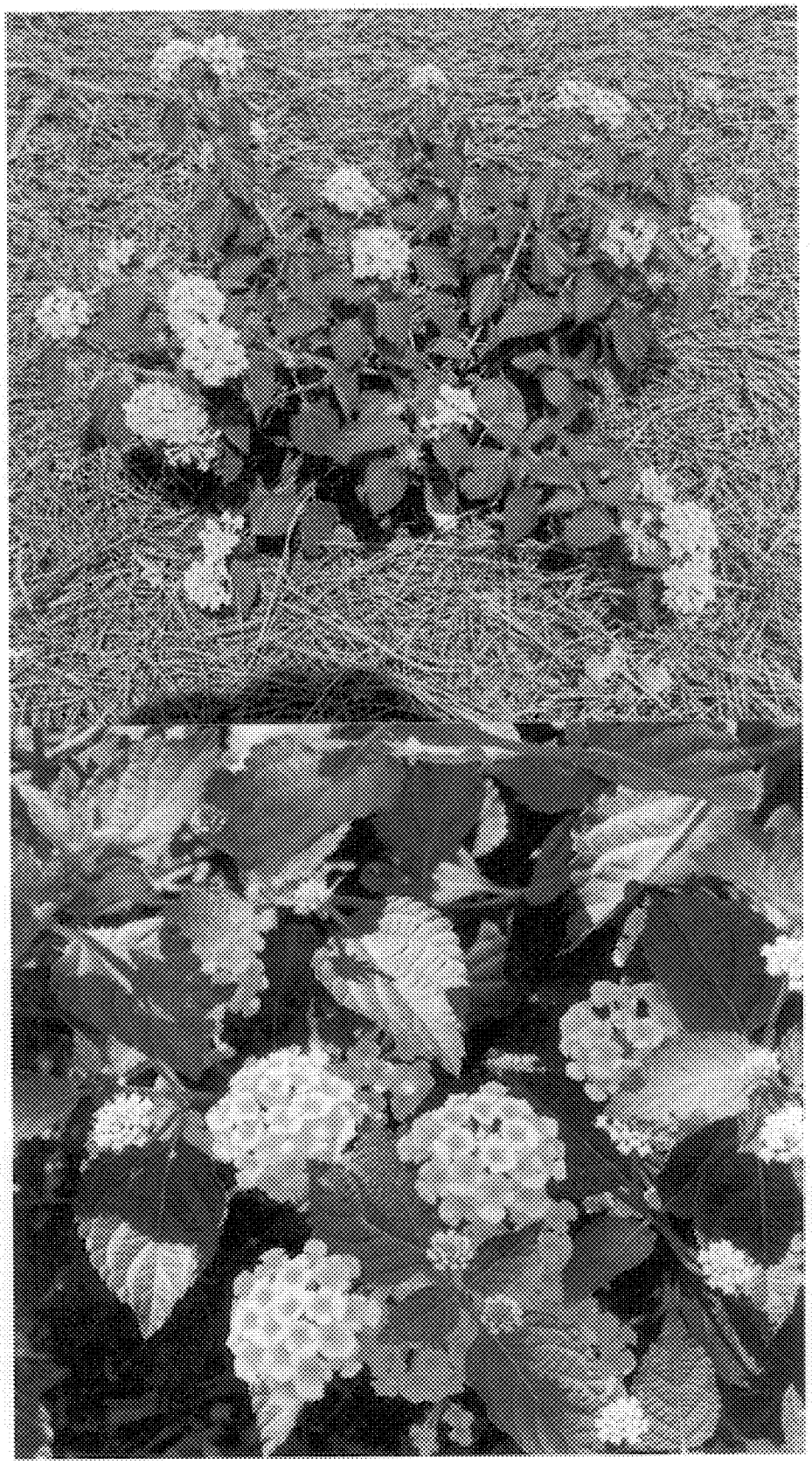

* * * * *